US008313697B2

(12) United States Patent
Sato

(10) Patent No.: US 8,313,697 B2
(45) Date of Patent: Nov. 20, 2012

(54) CARTRIDGE AND ANALYZING SYSTEM

(75) Inventor: Yoshiharu Sato, Kyoto (JP)

(73) Assignee: Arkray, Inc., Kyoto (JP)

( * ) Notice: Subject to any disclaimer, the term of this patent is extended or adjusted under 35 U.S.C. 154(b) by 415 days.

(21) Appl. No.: 12/312,330

(22) PCT Filed: Nov. 6, 2007

(86) PCT No.: PCT/JP2007/071522
§ 371 (c)(1),
(2), (4) Date: Mar. 24, 2010

(87) PCT Pub. No.: WO2008/056647
PCT Pub. Date: May 15, 2008

(65) Prior Publication Data
US 2010/0196201 A1 Aug. 5, 2010

(30) Foreign Application Priority Data
Nov. 6, 2006 (JP) ................................. 2006-300703

(51) Int. Cl.
*G01N 27/00* (2006.01)
*B65D 69/00* (2006.01)
(52) U.S. Cl. ...... 422/82.01; 422/68.1; 422/78; 422/401; 422/409; 422/544; 435/287.1; 436/131; 436/140; 436/151
(58) Field of Classification Search .................. 422/401, 422/554; 435/4; 436/150, 151; 206/223
See application file for complete search history.

(56) References Cited

U.S. PATENT DOCUMENTS
5,395,504 A 3/1995 Saurer et al.
5,797,693 A 8/1998 Jaeger
2005/0196747 A1 9/2005 Stiene
2008/0044879 A1* 2/2008 Harjes et al. ............... 435/173.6

FOREIGN PATENT DOCUMENTS
| JP | 06-294769 A | 10/1994 |
|---|---|---|
| JP | 2510702 Y2 | 6/1996 |
| JP | 08-302314 A | 11/1996 |
| JP | 09-021811 A | 1/1997 |
| JP | 2003-302314 A | 10/2003 |
| JP | 2005-249796 A | 9/2005 |
| TW | 455555 | 9/2001 |
| TW | 539555 | 7/2003 |
| WO | WO-2006/078016 A1 | 7/2006 |

OTHER PUBLICATIONS
International Search Report mailed on Feb. 12, 2008.
Office Action/Search Report from Taiwan Patent Office Action for application No. 096141884 dated Aug. 3, 2011.

* cited by examiner

*Primary Examiner* — In Suk Bullock
*Assistant Examiner* — Timothy G Kingan
(74) *Attorney, Agent, or Firm* — Rader, Fishman & Grauer PLLC

(57) ABSTRACT

The present invention relates to a cartridge 1 including a plurality of analyzing tools 3 arranged lined in a plane direction and a case 2 for accommodating the plurality of analyzing tools 3, and being configured to take out the analyzing tool 3 one at a time from the case 2. The plurality of analyzing tools 3 further include engagement means 32, 33 for restricting the analyzing tools 3 adjacent to each other in the plane direction and allowing removable attachment in a thickness direction D1, D2 of the analyzing tool 3. The present invention further relates to an analyzer and an analyzing system for analyzing a sample using the cartridge 1.

13 Claims, 14 Drawing Sheets

CARTRIDGE AND ANALYZING SYSTEM

TECHNICAL FIELD

The present invention relates to a cartridge equipped with a plurality of analyzing tools, and an analyzer for taking out the analyzing tool from the cartridge and analyzing a sample using such an analyzing tool.

BACKGROUND ART

An analyzing tool such as a biosensor is used when measuring a specific component in a sample such as blood. The analyzing tool is configured to be disposable, where such an analyzing tool is used by being attached to an analyzer.

The disposable analyzing tool generally has a capillary formed by joining a substrate and a cover by way of a spacer, where a reagent layer is provided in the interior of the capillary. Such an analyzing tool is desirably small in view of material cost, production equipment expense, production equipment installation area, transportation cost, convenience of the user in carrying around, and the like. However, if the analyzing tool is small, operability deteriorates when the user attaches the analyzing tool to the analyzer or detaches the used analyzing tool from the analyzer.

In order to enhance the operability of the user while miniaturizing the analyzing tool, there is known a configuration in which an analyzing tool is taken out one at a time from the cartridge accommodating a plurality of analyzing tools and attached to the analyzer. By way of example, the cartridge accommodating a plurality of analyzing tools is attached to the analyzer, and the operation unit arranged on the cartridge is operated to move the analyzing tool from the cartridge to the analyzer and attach the same thereto (see e.g., Patent Document 1). By way of another example, a cartridge holding a plurality of analyzing tools is incorporated in the analyzer, and a sample spotting portion in the analyzing tool is projected out from the analyzer in time of measurement (see e.g., Patent Document 2).

However, in the configuration of taking out the analyzing tool by operating the operation unit as in the cartridge described in Patent Document 1, the number of parts increases as the operation unit and the parts coupled thereto are necessary, and furthermore, the configuration of the cartridge becomes complicating. Thus, the manufacturing cost of the portion other than the analyzing tool in the cartridge becomes high even if the analyzing tool is miniaturized and the manufacturing cost is reduced.

In the configuration of accommodating a plurality of analyzing tools and projecting out the sample spotting portion of the desired analyzing tool to the outside of the analyzer as in the analyzer described in Patent Document 2, the device configuration becomes complicating and the manufacturing cost becomes high. Furthermore, the analyzer enlarges since a space for accommodating the plurality of analyzing tools needs to be ensured in the analyzer.

[Patent Document 1] Japanese Laid-Open Patent Publication No. 2003-302314

[Patent Document 2] Japanese Laid-Open Patent Publication No. 08-302314

DISCLOSURE OF THE INVENTION

Problems to be Solved by the Invention

The present invention aims to cost effectively miniaturize the analyzing tool while enhancing the operability of the user, and suppressing complication of the configuration of the cartridge and the analyzer, enlargement, and increase in number of parts.

Means for Solving the Problems

In a first aspect of the present invention, there is provided a cartridge including a plurality of analyzing tools arranged lined in a plane direction and a case for accommodating the plurality of analyzing tools, and being configured to take out the analyzing tool one at a time from the case; wherein the plurality of analyzing tools further include engagement means for restricting the analyzing tools adjacent to each other in the plane direction and allowing removable attachment in a thickness direction of the analyzing tool.

The engagement means includes, for example, a projecting portion projecting out in the thickness direction and a recessed portion to which the projecting portion can be inserted. The engagement means may include a projecting portion projecting out in a plane direction, and a recessed portion recessed in the plane direction.

The cartridge of the present invention preferably further includes holding means for putting an analyzing tool to be taken out in standby at a target position. The holding means includes, for example, a recessed portion arranged in the analyzing tool, and a hook arranged in the case.

The analyzing tool further includes, for example, an engagement portion utilized to act a load in a take-out direction on the analyzing tool when taking out from the cartridge. The engagement portion is, for example, a through-hole. The engagement portion may be a non-passing recessed portion or projecting portion.

The case further includes, for example, a slit for allowing movement of an acting body for acting a load on the engagement portion. The case preferably further includes a recessed portion for allowing displacement of a position in the thickness direction of the analyzing tool when the analyzing tool is relatively moved in a take-out direction with respect to the case.

In a second aspect of the present invention, there is provided an analyzer, attached with a cartridge accommodating a plurality of analyzing tools, for analyzing a sample using an analyzing tool taken out from the cartridge, where an analyzing tool further including an engagement portion utilized to act a load in a take-out direction on the analyzing tool is used as the analyzing tool of the cartridge, and a acting body for acting the load on the engagement portion is provided.

In a third aspect of the present invention, there is provided an analyzing system including: a cartridge having a plurality of analyzing tools arranged lined in a plane direction accommodated in a case; and an analyzer, attached with the cartridge, for analyzing a sample using the analyzing tool taken out from the cartridge; wherein the plurality of analyzing tools include engagement means for restricting the analyzing tools adjacent to each other in the plane direction and allowing removable attachment in a thickness direction of the analyzing tool, and an engagement portion utilized to act a load in a take-out direction on the analyzing tool when taking out from the cartridge; and the analyzer includes an acting body for acting on the engagement portion when taking out the analyzing tool from the cartridge.

The acting body reciprocates, for example, in the thickness direction of the analyzing tool, and is configured so as to be able to select a state the load can be acted on the engagement portion and a state the load cannot be acted. The engagement portion is a recessed portion such as a through-hole, and the acting body is a projecting portion such as a pin.

DESCRIPTION OF SYMBOLS

1 Cartridge
2 Case
24 Recessed portion (of case)
25 Hook (holding means)
3, 7 Biosensor (analyzing tool)
32 Engagement projection (projecting portion of engagement means)
33 Engagement hole (recessed portion of engagement means)
34 Through-hole (lock portion)
35 Cutout (holding means)
6 Analyzer
68B Pin (acting body)
68C Projection (pressing body)
N1, N2 Plane direction
D1, D2 Thickness direction (of biosensor)

BEST MODE FOR CARRYING OUT THE INVENTION

The present invention will be specifically described below with reference to the drawings.

Figure 1:
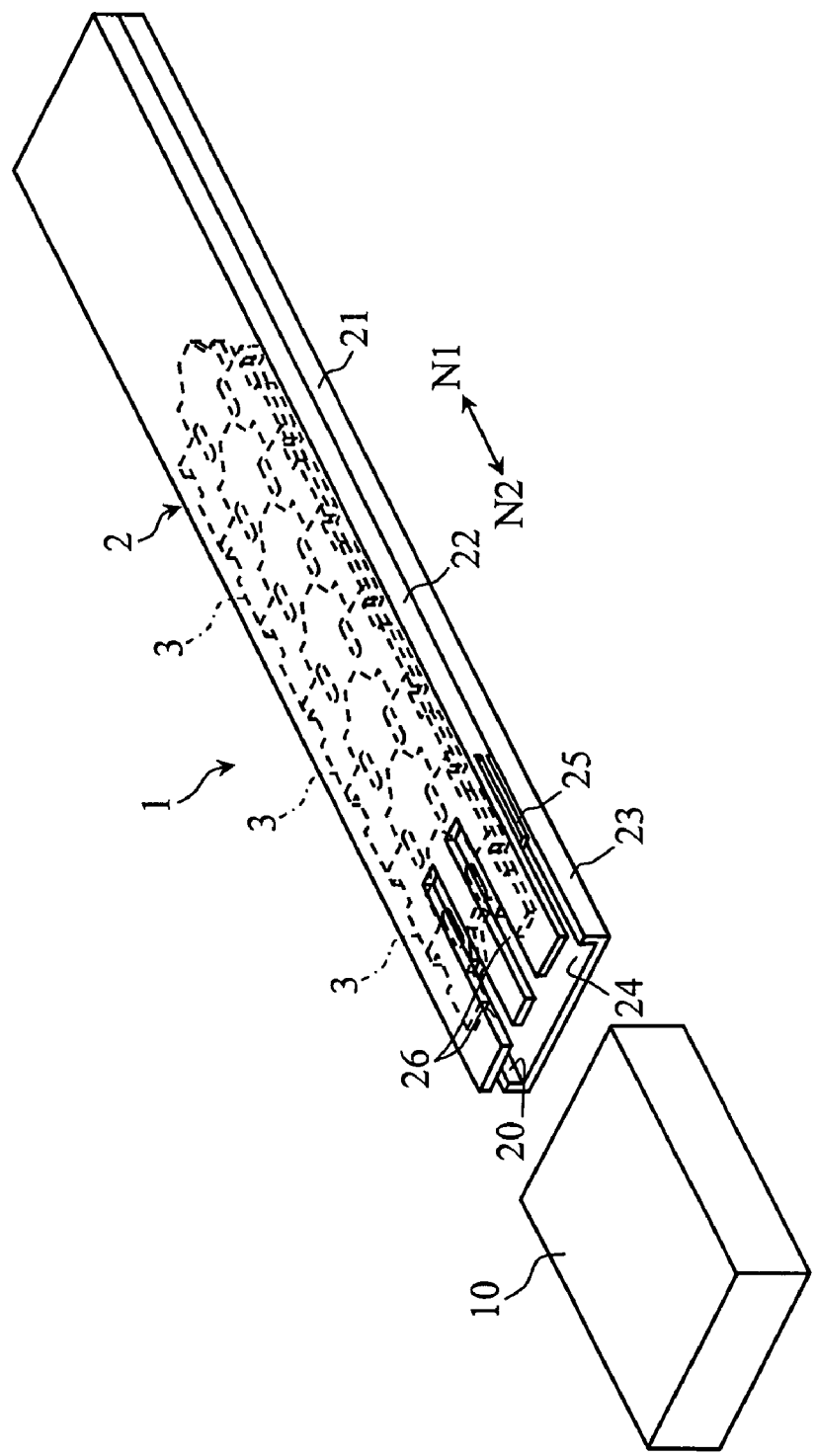
FIG. 1 is an overall perspective view showing one example of a cartridge according to the present invention.
Figure 2:
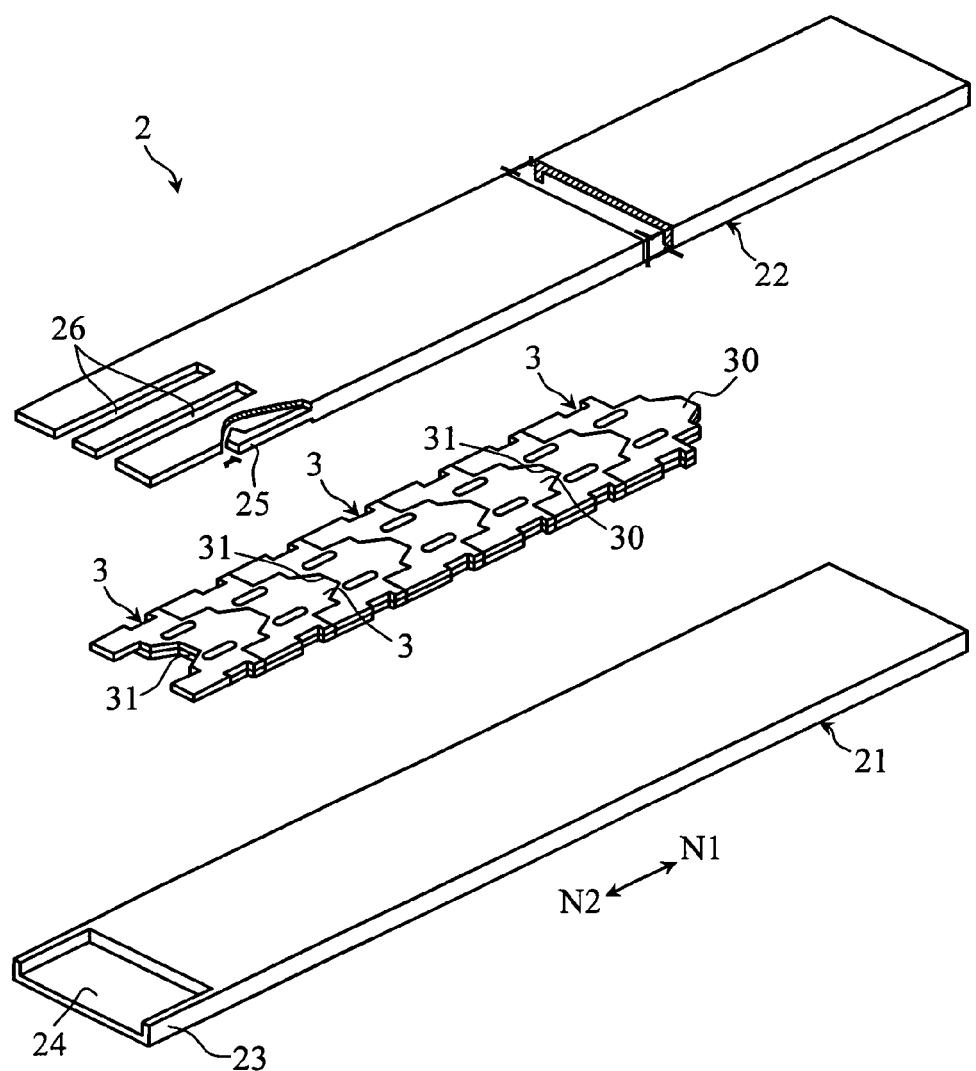
FIG. 2 is a perspective view showing the cartridge shown in FIG. 1 with a case in an exploded manner.

A cartridge 1 shown in FIGS. 1 and 2 accommodates a plurality of biosensors 3 in a case 2, where the biosensor 3 is taken out one at a time from the plurality of biosensors 3 for use.

Figure 10A:
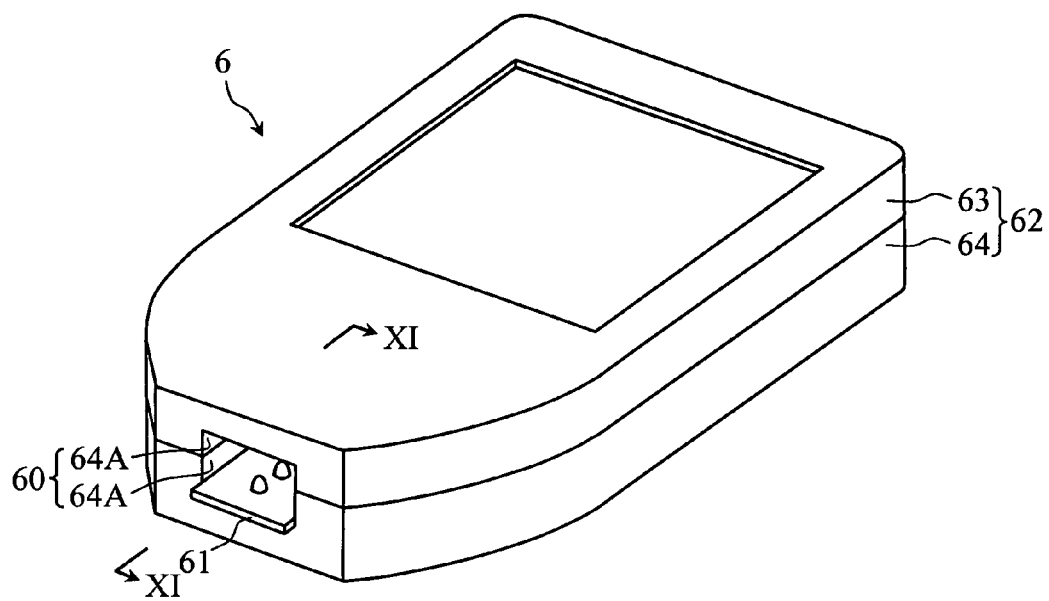
FIG. 10A is an overall perspective view showing one example of an analyzer according to the present invention.

As shown in FIGS. 2 to 5, the biosensor 3 is used to analyze a specific component (e.g., glucose, cholesterol, or lactic acid) in a sample such as blood and urine by being attached to an analyzer 6 (see FIGS. 10A and 10B), to be hereinafter described. The biosensor 3 is adapted to analyze a sample through electrochemical method, and is formed into a plate-shape as a whole. The plurality of biosensors 3 are arranged lined in a longitudinal direction N1, N2 of the case 2 in the cartridge 1. Each biosensor 3 has a projecting portion 30, a recessed portion 31, a pair of engagement projections 32, a pair of engagement holes 33, a pair of through-holes 34, and a pair of cutouts 35.

The projecting portion 30 is the portion (see FIG. 10B) that projects out from the analyzer 6 when the biosensor 3 is attached to the analyzer 6, and is the portion used when spotting and applying the sample to the biosensor 3. The recessed portion 31 is the portion for positioning the projecting portion 30 of the adjacent other biosensor 3 in the cartridge 1. In other words, the plurality of biosensors 3 can be accommodated in a space efficient manner in the cartridge 1 by lining the biosensors 3 with the projecting portion 30 positioned in the recessed portion 31.

Figure 6:
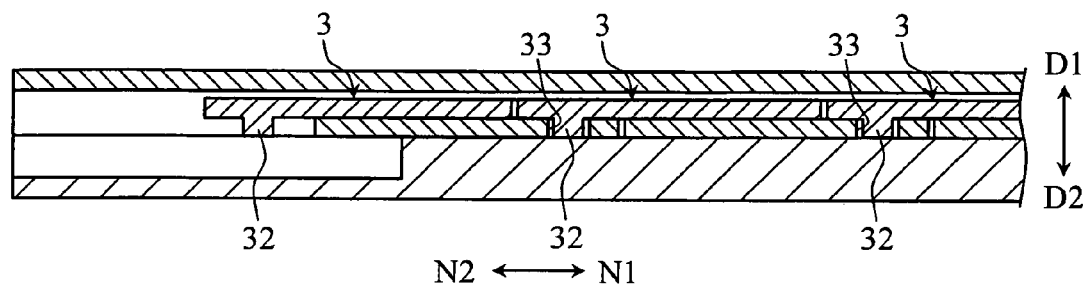
FIG. 6 is a cross-sectional view showing the main parts for describing a coupling state of a plurality of biosensors in a cartridge.

As shown in FIG. 6, the pair of engagement projections 32 engage the engagement hole 33 of the adjacent other biosensor 3. The adjacent biosensors 3 can be coupled to each other by engaging the engagement projections 32 to the engagement hole 33 of the adjacent biosensor 3. In this case, the adjacent biosensors 3 are restricted with respect to each other in the longitudinal direction N1, N2, and, on the other hand, are removably attached on the lower side in a thickness direction D1, D2.

Figure 3:
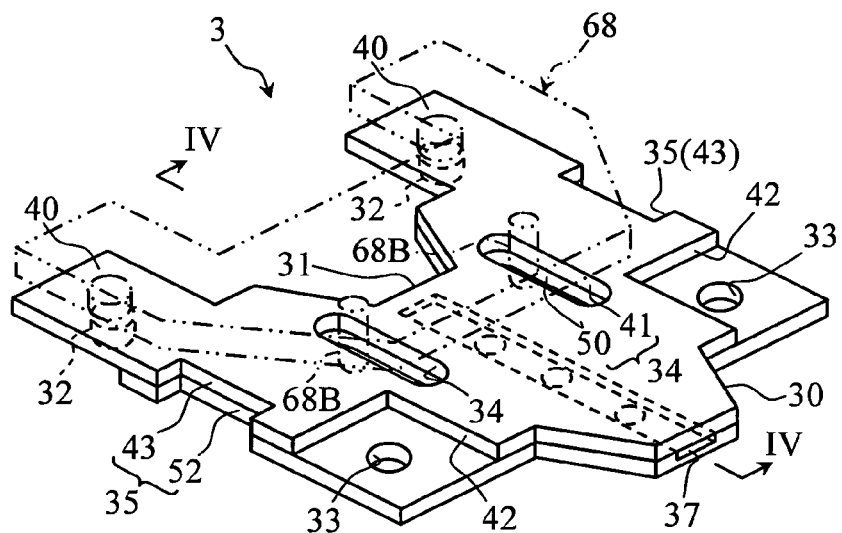
FIG. 3 is an overall perspective view of a biosensor of the cartridge shown in FIG. 1.

As shown in FIG. 3, the pair of through-holes 34 are used when taking out the biosensor 3 from the cartridge 1, and are the portion to be inserted with a pin 68B of a movable body 68 in the analyzer 6, to be hereinafter described.

Figure 7:
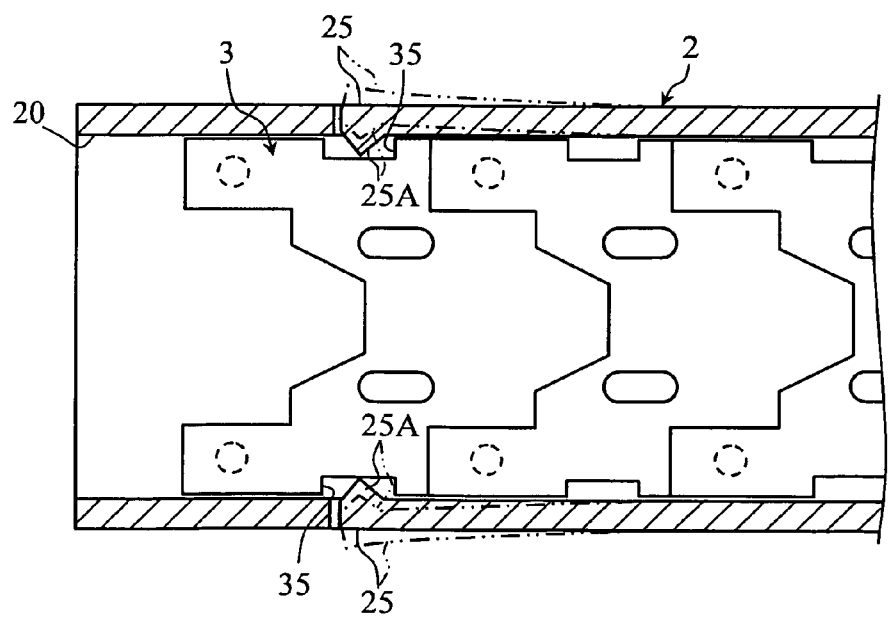
FIG. 7 is a cross-sectional view showing the main parts for describing a hook in the cartridge.

As shown in FIG. 7, the pair of cutouts 35 hold the biosensor 3 to be taken out at a predetermined position in the cartridge 1, and prevent the biosensor 3 from improperly coming out from a take-out port 20 (see FIG. 1) of the cartridge 1. The pair of cutouts 35 are the portion to which a hook 25 of the case 2 engages.

Figure 4:
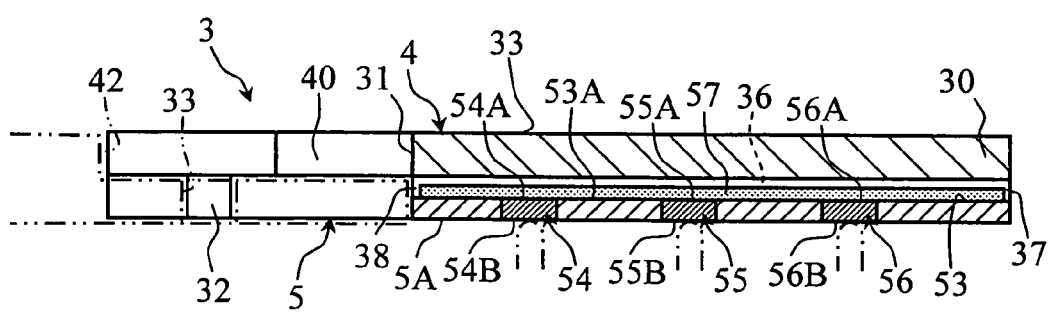
FIG. 4 is a cross-sectional view taken along line IV-IV of FIG. 3.
Figure 5:
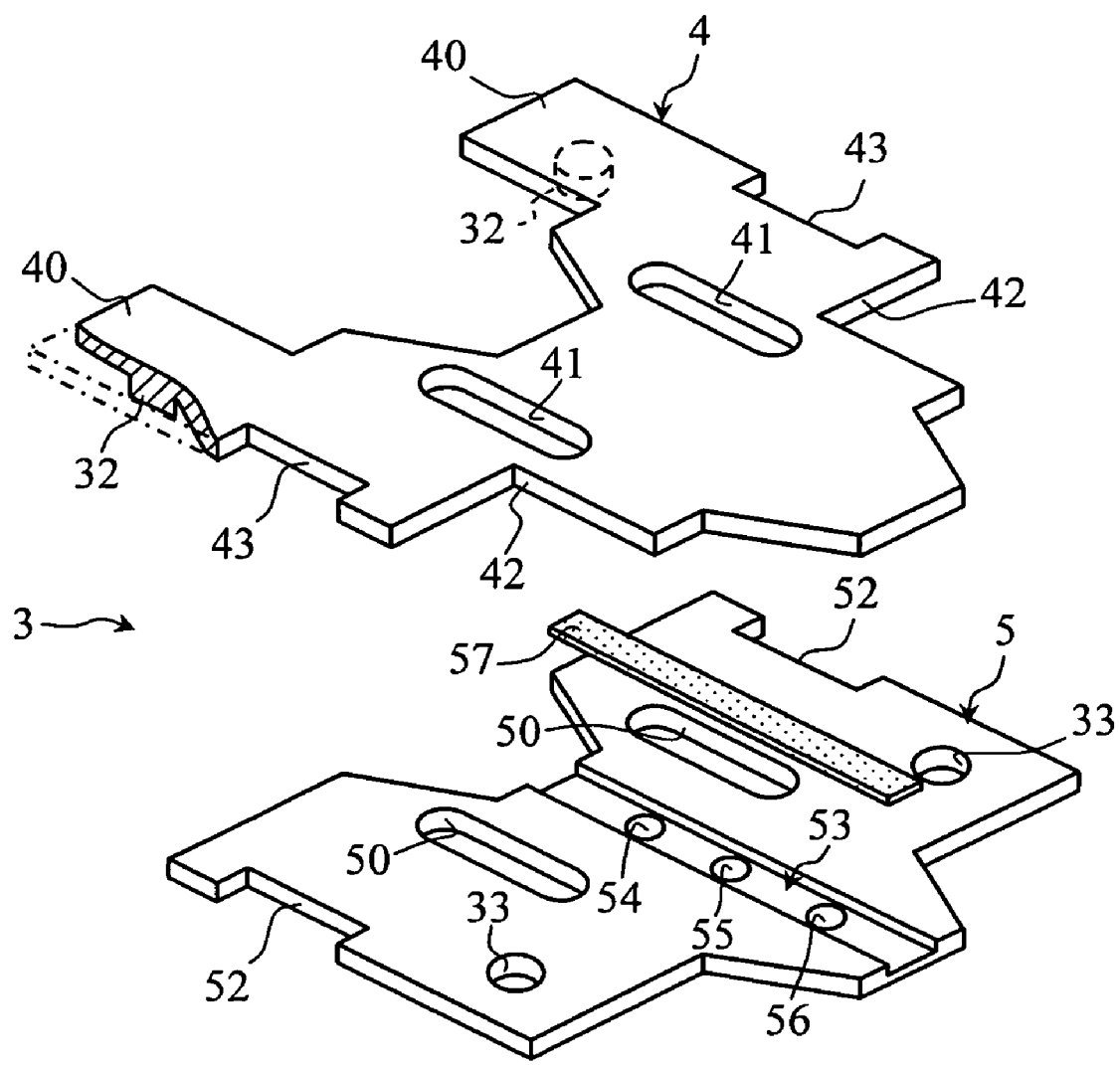
FIG. 5 is an exploded perspective view of the biosensor shown in FIG. 3.

As shown in FIGS. 3 to 5, the biosensor 3 is formed by joining a second plate material 5 to a first plate material 4 by way of an adhesive and the like.

The first plate material 4 is made of an insulating resin material such as PET, and includes a pair of flanges 40, a pair of through-holes 41, and cutouts 42, 43.

The pair of flanges 40 are the portion to be positioned at the cutout 42 of the other first plate material 5, and are arranged projecting out with respect to the second plate material 5. Such flanges 40 have an engagement projection 32 arranged projecting downward.

The pair of through-holes 41 configure the through-hole 34 in the biosensor 3, and are formed into an oval shape.

The cutout 42 is the portion for exposing the engagement hole 33 of the second plate material 5, to be hereinafter described, and positioning the flange 40 of the first plate material 4 in another biosensor 3. The plurality of biosensors 3 can be accommodated in a space efficient manner in the cartridge 1 by positioning the flange 40 of another biosensor 3 in the cutout 42 (see FIGS. 1 and 2).

The cutouts 43 configure the cutouts 35 of the biosensor 3, and are arranged on both sides of the first plate material 4.

The second plate material 5 is made of an insulating resin material such as PET as in the first plate material 4, and includes a pair of through-holes 50, a pair of engagement holes 33, a pair of cutouts 52, and a groove 53.

The pair of through-holes 50 configure the through-hole 34 of the biosensor 3, and are provided at positions corresponding to the pair of through-holes 41 of the first plate material 4.

As described above, the pair of engagement holes 33 are engaged with the engagement projection 32 of the first plate material 4 in another biosensor 3, and are exposed by the cutout 42 of the first plate material 4.

The pair of cutouts 52 configure the cutout 35 of the biosensor 3, and are arranged on both sides of the second plate material 5 in correspondence to the cutout 43 of the first plate material 4.

The groove 53 moves the sample such as blood supplied to the biosensor 3. The groove 53 configures a capillary 36 when the second plate material 5 is stacked on the first plate material 4. The capillary 36 is opened at both ends so that capillary force can act. The capillary 36 is introduced with a sample from an end 37, and the sample is moved towards an end 38 by the capillary force in the capillary 36.

The second plate material 5 is arranged with a working electrode 54, a counter electrode 55, a detection electrode 56, and a reagent layer 57.

The working electrode 54 performs electron exchange with the specific component in the sample. The counter electrode 55 applies voltage in between the working electrode 54. The detection electrode 56 detects the supply of sample to the capillary 36. The detection electrode 56 detects the supply of sample to the capillary 36 by detecting the current in the case where liquid junction occurs with the working electrode 54 or the counter electrode 55 by the sample.

Such electrodes 54 to 56 are formed into a columnar shape, where the end faces 54A, 55A, and 56A are exposed on a bottom surface 53A of the groove 53, and the end faces 54B, 55B, and 56B are exposed on a bottom surface 5A of the second plate material 5. The end faces 54B, 55B, and 56B are portions to which a pin-shaped terminal 69 of the analyzer 6, to be hereinafter described, is contacted (see FIG. 21).

The electrodes 54 to 56 can be formed by inserting a columnar conductor when resin molding the second plate material 5. Various known types generally used for the electrode material can be used for the material of the electrodes 54 to 56. Such a material includes carbon and the like in addition to a noble metal such as gold, silver and platinum. The material of the electrodes 54 to 56 may also be that given conductivity by adding metal powder and the like in the resin. The electrodes 54 to 56 may be formed by forming a through-hole in the second plate material 5, and filling conductor component in the through-hole by screen printing and the like or covering a conductor layer on the through-hole by electroless plating and the like.

The working electrode, the counter electrode, and the detection electrode do not necessarily need to be formed lined in the illustrated order, and the detection electrode may be arranged at the farthest when seen from the end 37 of the capillary 36 or the detection electrode may be omitted.

The reagent layer 57 is formed into a solid form that melts when the sample is supplied, and contains, for example, oxidoreductase and an electron transfer substance. The type of oxidoreductase is selected according to the component to be analyzed, where glucose dehydrogenase or glucose oxidase is used when measuring the glucose concentration. Various known types can be used for the electron transfer substance, and for example, Ru complex ($[Ru(NH_3)_6Cl_3]$ etc.) and Fe complex ($[K_3(CN)_6]$ etc.) may be used.

As shown in FIGS. 1 and 2, the case 2 accommodates the plurality of biosensors 3, and includes the take-out port 20. The take-out port 20 is provided to take out the biosensor 3 and can be blocked by a cap 10. Such a case 2 is formed by attaching a cover 22 to a base 21.

Figure 8:
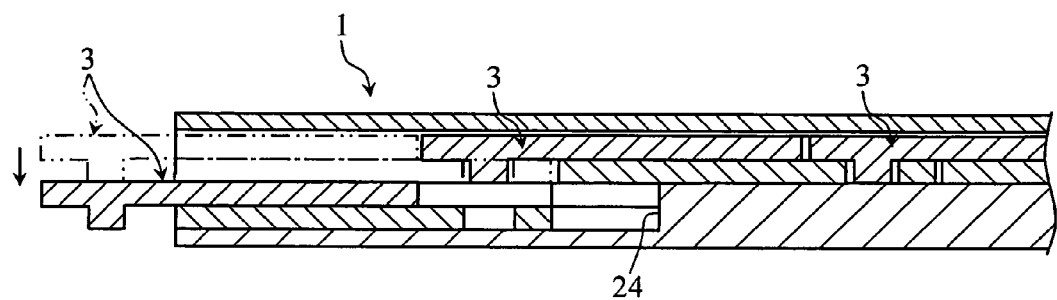
FIG. 8 is a cross-sectional view showing the main parts for describing a recessed portion in the cartridge.

The base 21 is formed into a rectangular shape by resin such as PET, where a recessed portion 24 is formed at an end 23. As shown in FIG. 8, the recessed portion 24 is the portion where the biosensor 3 to be taken out is positioned when the biosensor 3 to be taken out and the adjacent biosensor 3 are disengaged.

As shown in FIGS. 1 and 2, the cover 22 defines a space for accommodating the plurality of biosensors 3 with the base 21. The cover 22 includes a pair of hooks 25 and a pair of slits 26.

As shown in FIG. 7, the pair of hooks 25 engage the cutout 35 of the biosensor 3. The hook 25 has spring property such that a projecting portion 25A can swing.

Figure 9:
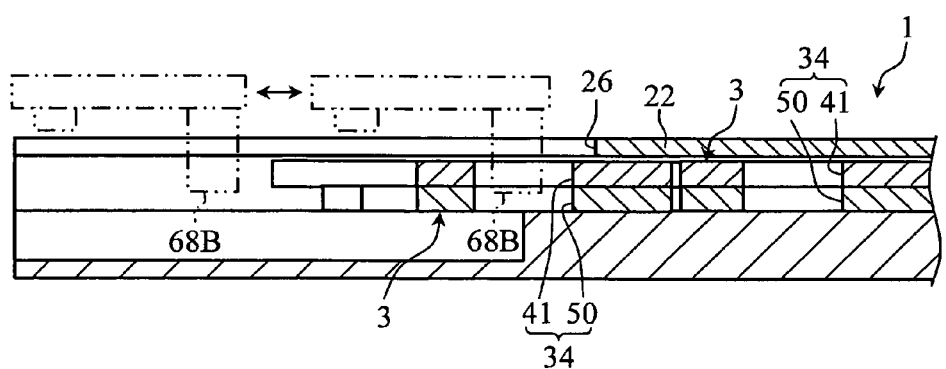
FIG. 9 is a cross-sectional view showing the main parts for describing a slit in the cartridge.

As shown in FIG. 9, the pair of slits 26 are used when taking out the biosensor 3 from the cartridge 1, and are passed through in the thickness direction of the cover 22. More specifically, each slit 26 allows a pair of pins 68B in the analyzer 6 to be inserted to the through-holes 34 (41, 50) of the biosensor 3, and allows the pair of pins 68B to relatively move with respect to the cartridge 1 (cover 22) with the pair of pins 68B inserted in the through-holes 34 (41, 50).

The analyzer used with the cartridge 1 will be described with reference to FIGS. 10 to 12.

As shown in FIG. 10, the analyzer 6 analyzes the sample using the biosensor 3 of the cartridge 1 (see FIGS. 1 and 13), and includes an insertion port 60. The insertion port 60 is inserted with the end of the cartridge 1, and is arranged with a guide 61 at a lower position thereof.

The analyzer 6 has the outer appearance shape defined by a housing 62. The housing 62 includes an upper case 63 and a lower case 64, where the insertion port 60 is formed by cutouts 63A, 63B of the cases 63, 64.

Figure 11:
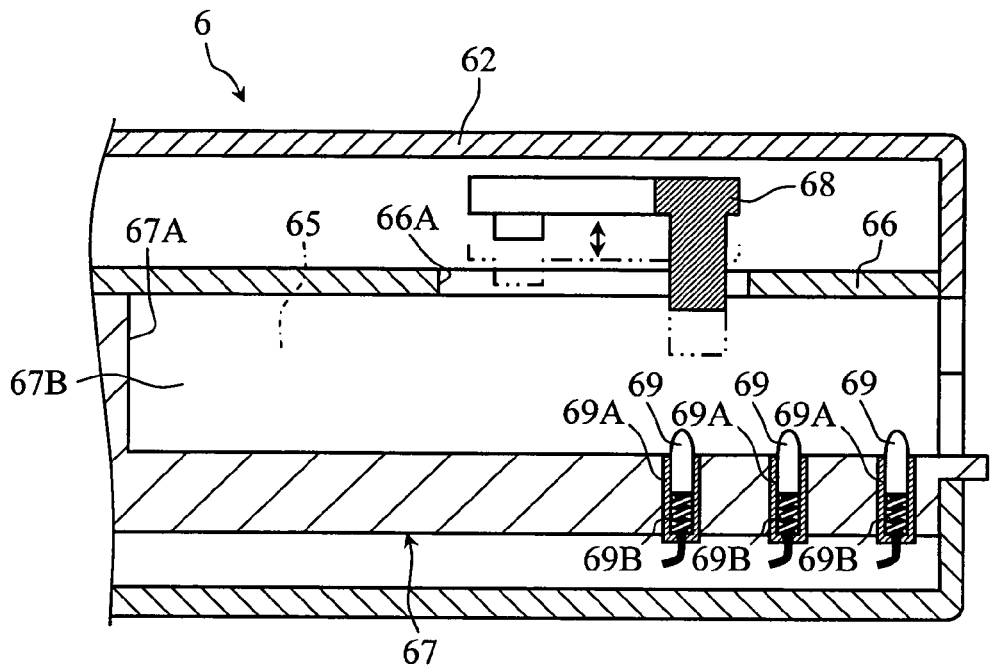
FIG. 11 is a cross-sectional view taken along line XI-XI of FIG. 10A.

As shown in FIG. 11, a space 65 for inserting the end of the cartridge 1 is formed inside the housing 62. The space 65 is defined by a plate 66 and a base block 67.

The plate 66 is arranged to cover the base block 67, and includes a slit 66A. The slit 66A allows the up and down movement of the movable body 68.

Figure 12:
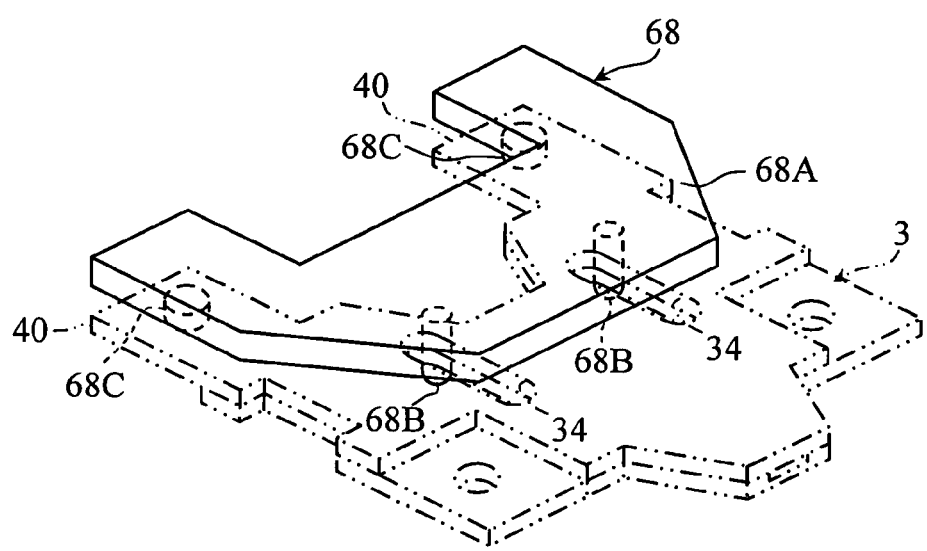
FIG. 12 is a perspective view for describing a movable body in the analyzer shown in FIG. 10A.

The movable body 68 takes out the biosensor 3 from the cartridge 1 or fixes the biosensor 3 in the analyzer 6, where the pair of pins 68B and a pair of projections 68C project out from a base plate 68A as shown in FIG. 12.

The pair of pins 68B are inserted to the pair of through-holes 34 in the biosensor 3 of the cartridge 1. In other words, the biosensor 3 can be taken out from the cartridge 1 and retained in the space 65 of the analyzer 6 by detaching the cartridge 1 from the analyzer 6 with the pin 68B inserted in the through-hole 34 (see FIGS. 20 and 21).

The pair of projections 68C fix the biosensor 3 in the analyzer 6. In other words, the projection 68C can fix the biosensor 3 in the analyzer 6 by pressing the flange 40 of the biosensor 3.

Such a movable body 68 can reciprocate in the up and down direction by an actuator, a link mechanism, and the like (not shown), and takes a position at which the pin 68B is not inserted to the through-hole 34, a position at which the pin 68B is inserted to the through-hole 34 and the projection 68C does not press the flange 40, and a position at which the projection 68C presses the flange 40. The movable body 68 may obviously be configured to reciprocate in the up and down direction by hand.

As shown in FIG. 11, the base block 67 includes a recessed portion 67A, and can define an insertion depth of the cartridge 1 by the interference of the cartridge 1 with an inner surface 67B. The base block 67 is fixed with three pin-shaped terminals 69.

Figure 21:
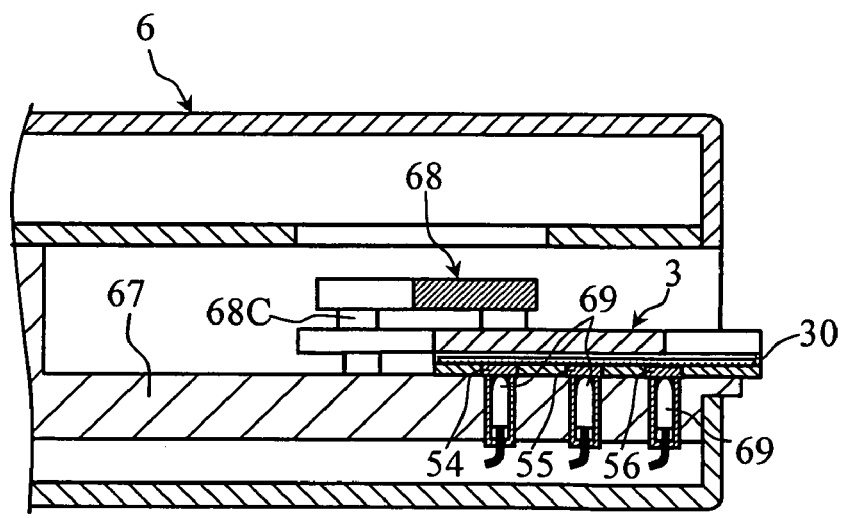
FIG. 21 is a cross-sectional view showing the main parts for describing the operation of the analyzer.

The three pin-shaped terminals 69 contact the electrodes 54 to 56 of the biosensor 3 (see FIG. 21). Each pin-shaped terminal 69 is biased upward by a coil spring 69B while being fitted inside a cylinder 69A, and is movable in the up and down direction.

The analyzing operation of the sample using the cartridge 1 and the analyzer 6 will now be described with reference to FIGS. 13 to 21.

Figure 13:
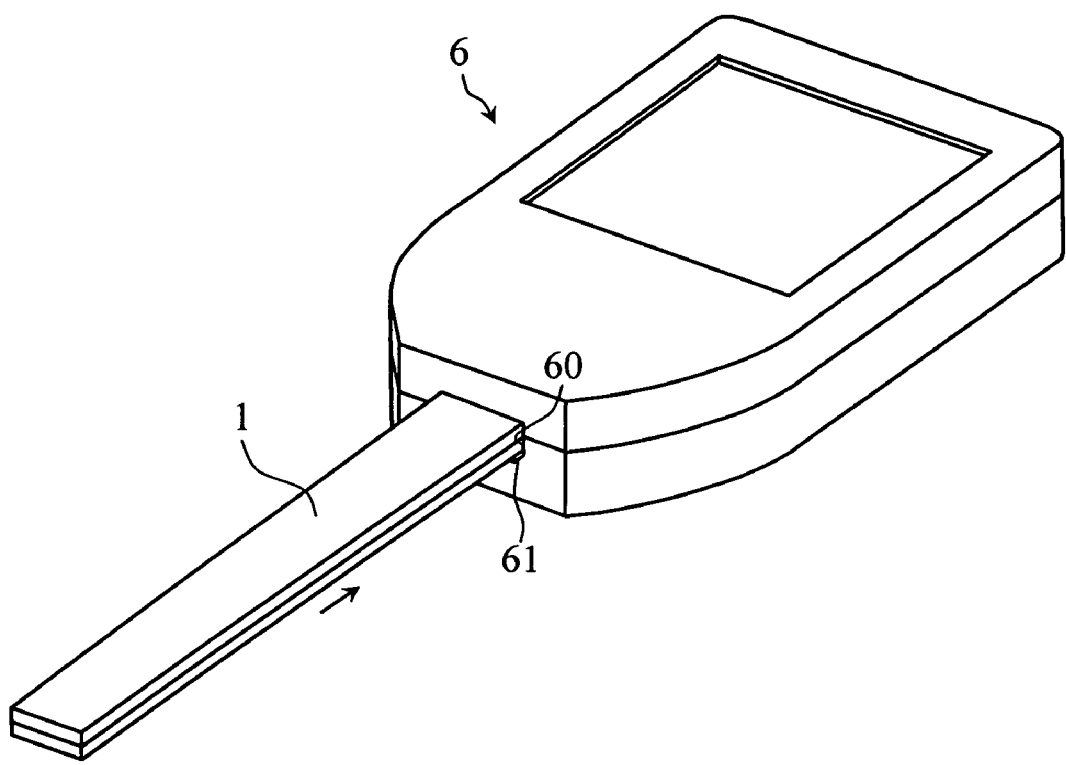
FIG. 13 is a perspective view for describing the operation of the analyzer and the cartridge.
Figure 14:
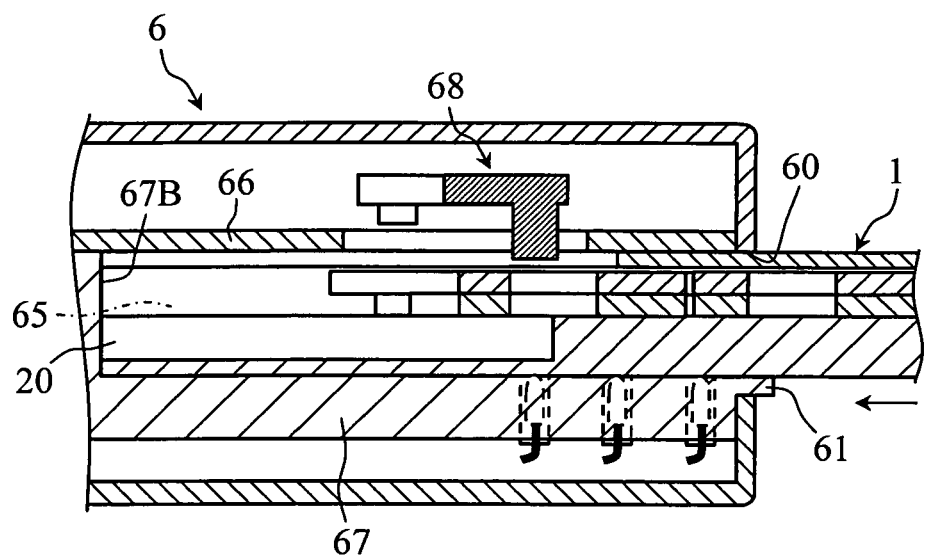
FIG. 14 is a cross-sectional view showing the main parts for describing the operation of the analyzer and the cartridge.

As shown in FIGS. 13 and 14, the cartridge 1 is first attached to the analyzer 6 to analyze the sample using the analyzer 6. The cartridge 1 is attached to the analyzer 6 by inserting the take-out port 20 to the space 65 from the insertion port 60 of the analyzer 6. In this case, the cartridge 1 can be smoothly attached to the analyzer 6 since the guide 61 is formed at the analyzer 6. When the cartridge 1 is inserted to the analyzer 6, the cartridge 1 interferes with the inner surface 67B of the base block 67 thereby regulating the insertion depth of the cartridge 1.

Figure 15:
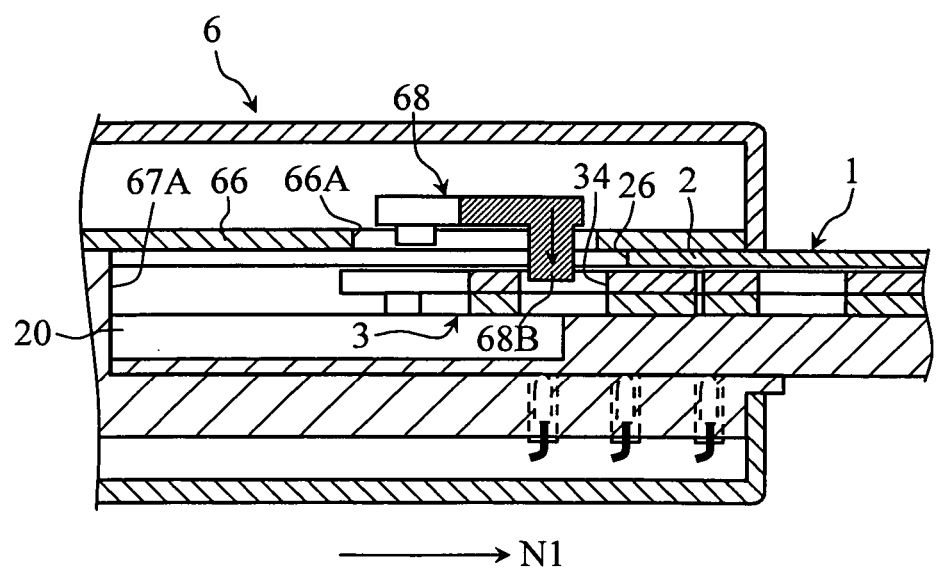
FIG. 15 is a cross-sectional view showing the main parts for describing the operation of the analyzer and the cartridge.

The movable body 68 is then moved downward, as shown in FIGS. 14 and 15. In this case, since the slits 26, 66A are formed in the case 2 and the plate 66, the pin 68B of the movable body 68 is inserted to the through-hole 34 of the biosensor 3 at the farthest end held in the hook 25 of the cartridge 1, as shown in FIGS. 15 and 16.

Figure 16:
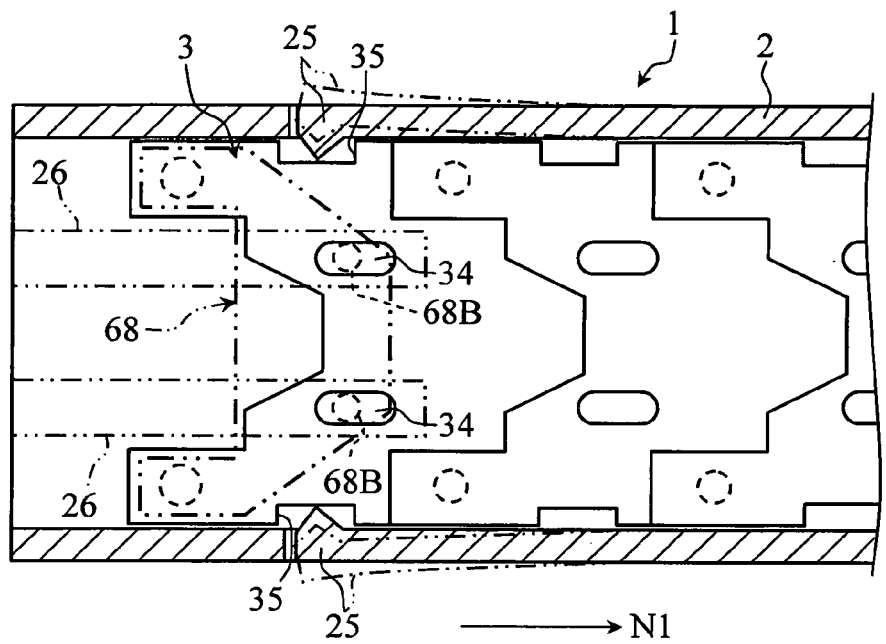
FIG. 16 is a cross-sectional view for describing the operation of the cartridge.
Figure 17:
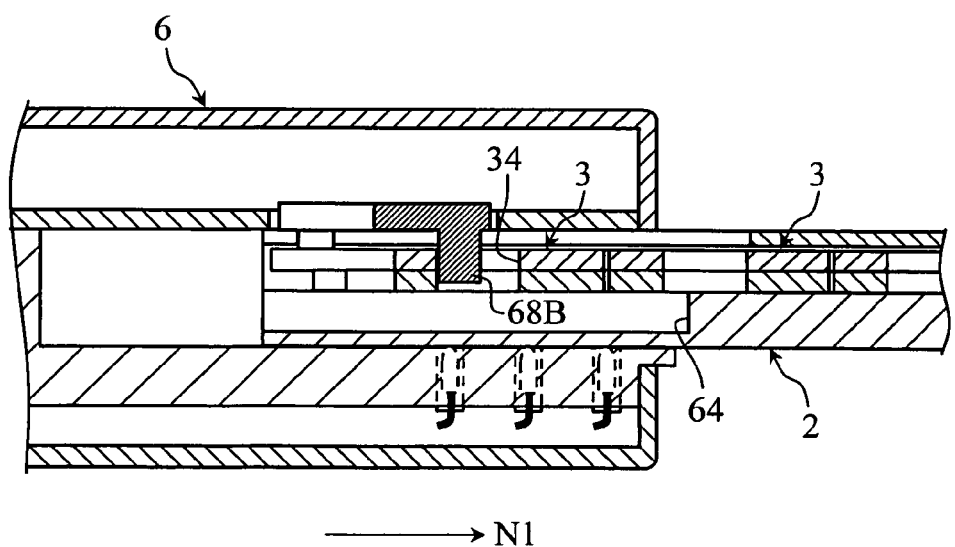
FIG. 17 is a cross-sectional view showing the main parts for describing the operation of the analyzer and the cartridge.
Figure 18:
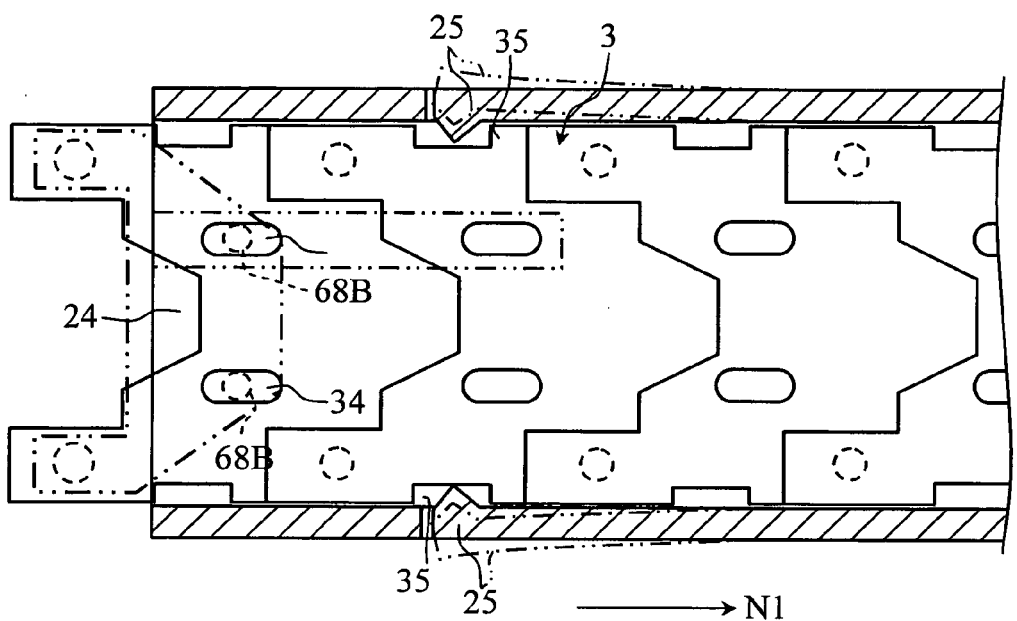
FIG. 18 is a cross-sectional view for describing the operation of the cartridge.
Figure 19:
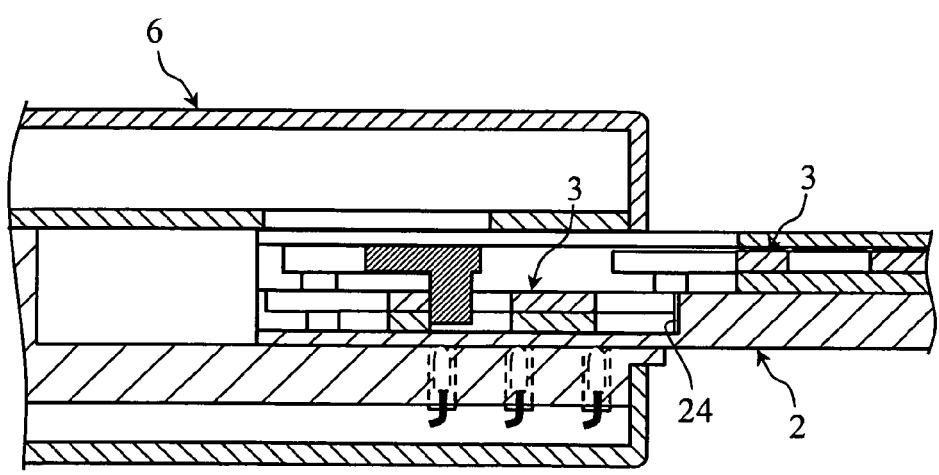
FIG. 19 is a cross-sectional view showing the main parts for describing the operation of the analyzer and the cartridge.

The cartridge 1 is then moved in a direction N1 of moving away from the analyzer 6, as shown in FIGS. 16 and 17. In this case, the biosensor 3 at the farthest end cannot move since the biosensor 3 has the pin 68B inserted to the through-hole 34. Thus, the hook 25 elastically deforms and displaces to the outer side by the movement force of the case 2 towards the N1 direction, and the hook 25 separates from the cutout 35 of the biosensor 3. The case 2 is then moved in the N1 direction independent from the biosensor 3, as shown in FIGS. 18 and 19.

The plurality of biosensors 3 have the adjacent biosensors 3 coupled by the engagement projection 32 and the engagement hole 33 (see FIG. 6), and thus the plurality of biosensors 3 relatively move in the N2 direction with respect to the case 2 when the case is moved in the N1 direction. When the case 2 is moved by a constant distance with respect to the plurality of biosensors 3, the biosensor 3 is positioned at the recessed portion 24 of the case 2, and the biosensor 3 is displaced to the lower side and freed from the other biosensor 3. Meanwhile, the hook 25 of the case 2 engages the cutout 35 of the biosensor 3, and the biosensor 3 to be taken out next is held at a standby position.

Figure 20:
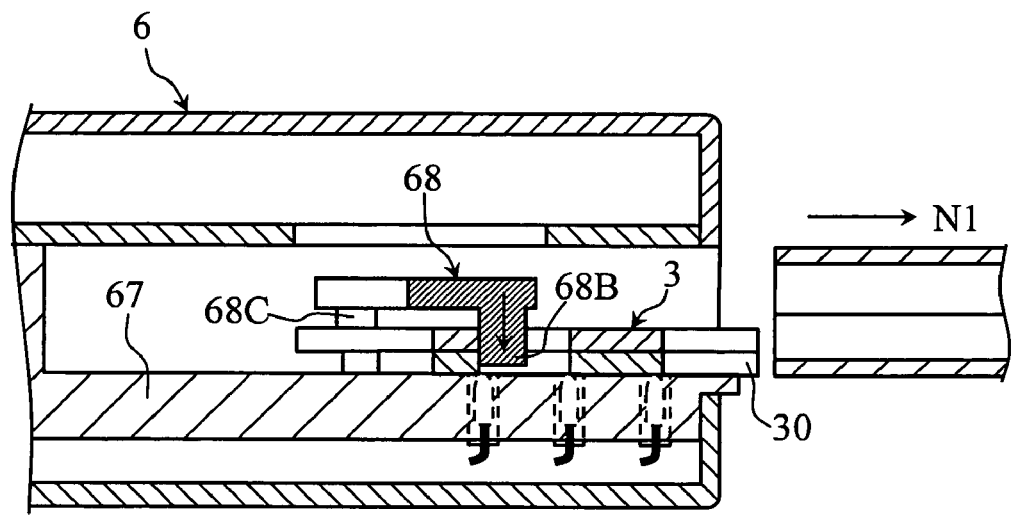
FIG. 20 is a cross-sectional view showing the main parts for describing the operation of the analyzer.

As shown in FIG. 20, the movable body 68 is further moved downward. The force directed downward acts on the biosensor 3. Thus, even if not sufficiently freed with respect to the biosensor 3 to be taken out next, the biosensor 3 is reliably separated from the biosensor 3 by the pressing force of the movable body 68. The biosensor 3 is then pressed against the base block 67 by the projection 68C of the movable body 68.

Figure 10B:
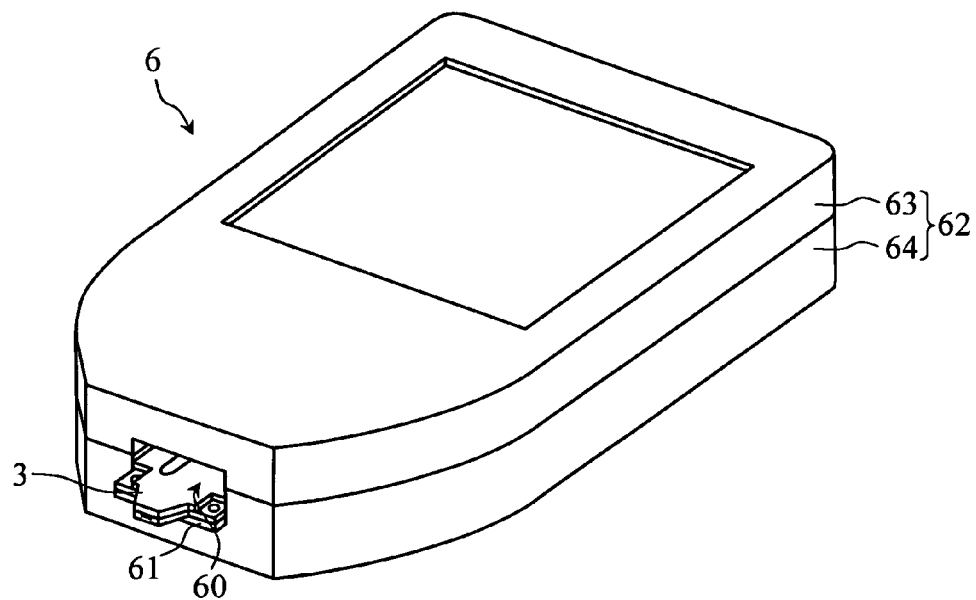
FIG. 10B is an overall perspective view showing a state in which the biosensor is attached to the analyzer.

The biosensor 3 is thereby held in the analyzer 6. In this case, as shown in FIGS. 10B and 20, the projecting portion 30 of the biosensor 3 is projects out from the analyzer 6, and each pin-shaped terminal 69 contacts the electrodes 54 to 56 of the biosensor 3, as shown in FIG. 21.

When analyzing the sample, the user spots and applies the sample to the projecting portion 30 of the biosensor 3 (end 37 of capillary 36). The spot application of the sample is carried out by cutting the skin of the subject and bleeding blood and spotting and applying the blood to the biosensor 3, or by spotting and applying the sample such as urine collected in advance to the projecting portion 30 of the biosensor 3 using an appropriate spotter. When the sample is spotted and applied to the projecting portion 30 of the biosensor 3, the sample moves towards the end 38 by the capillary force in the capillary 36, and the reagent layer 57 inside the capillary 36 melts by the sample (see FIG. 4).

In the analyzer 6, whether or not the sample is supplied to the capillary 36 of the biosensor 3 is determined. This determination is made by applying voltage through the pin-shaped terminal 69 between the detection electrode 56 and the working electrode 54 (or counter electrode 55), and by electrically detecting whether or not liquid junction occurred between the detection electrode 56 and the working electrode 54 (or counter electrode 55).

When determined that the blood is supplied to the capillary 36 in the analyzer 6, the voltage is applied through the pin-shaped terminal 69 between the working electrode 54 and the counter electrode 55, and the response current in such a case is measured. The response current is correlated to the electron exchange amount between the specific component in the sample and the working electrode 54, and thus the concentration of the specific component in the sample can be calculated by the response current.

In the analyzer 6, the response current after elapse of a constant time from the application of voltage between the working electrode 54 and the counter electrode 55 is sampled, and the concentration of the specific component in the sample is calculated based on the response current value in such a case. This calculation is carried out by applying the sampled response current value to the analytical curve or the correspondence table created in advance.

When the analysis of the sample is terminated in the analyzer 6, the movable body 68 is moved upward, and the pressing force acting on the biosensor 3 is released (see FIG. 14). The biosensor 3 is then freed with respect to the analyzer 6, and thus, the user can discard the biosensor 3 from the analyzer 6 without touching the biosensor 3 by simply moving the analyzer 6 to above a discard box, and directing the insertion port 60 of the analyzer 6 downward.

The above-described cartridge 1 is configured to take out the biosensor 3 using the pin 68B of the analyzer 6. Thus, in the cartridge 1, a mechanism for taking out the biosensor 3 is not required, and the user can attach the biosensor 3 to the analyzer 6 without touching the biosensor 3. Thus, the configuration of the cartridge 1 can be simplified, and the biosensor 3 can be miniaturized since a gripping portion of the user does not need to be provided with respect to the biosensor 3. As the configuration of the cartridge 1 is simplified and the biosensor 3 is miniaturized, the cartridge 1 can be miniaturized. In the cartridge 1, the thickness of the cartridge 1 can be significantly reduced since the plurality of biosensors 3 are arranged lined in the plane direction.

The analyzer 6 can take out the biosensor 3 from the cartridge 1 by the movable body 68 movable in the up and down direction, and hold the biosensor 3 in the analyzer 6. The movable body 68 has an extremely simple configuration equipped with the pin 68B for engaging the biosensor 3 of the cartridge 1 and the projection 68C for pressing the biosensor 3. Thus, the configuration of the analyzer 6 does not become as complicated and the analyzer 6 does not becomes as large even if a mechanism for taking out the biosensor 3 from the cartridge 1 is arranged in the analyzer 6.

Another example of the biosensor applicable in the cartridge according to the present invention will be described with reference to FIGS. 22A and 22B, where in FIGS. 22A and 22B, like reference numerals are denoted for elements having similar functions as in the biosensor (see FIGS. 3 to 5) described above, and the redundant description will not be given.

Figure 22A:
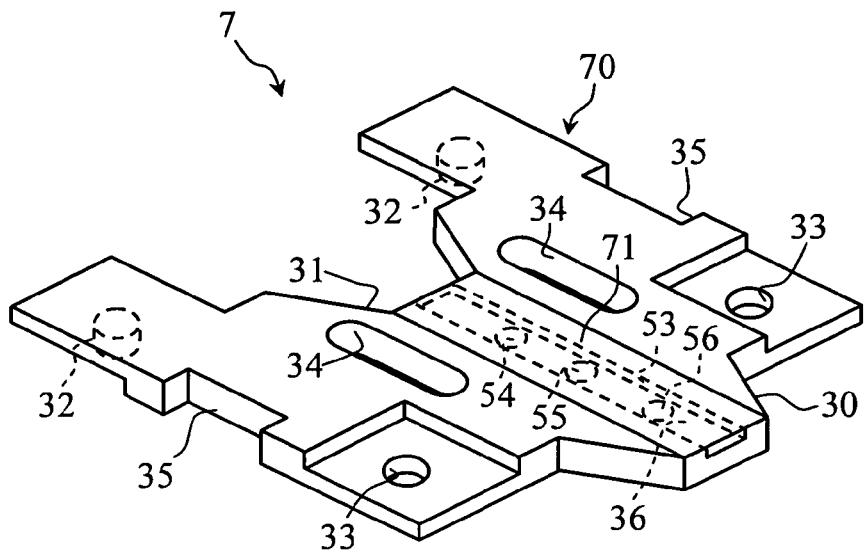
FIG. 22A is a perspective view for describing another example of a biosensor.
Figure 22B:
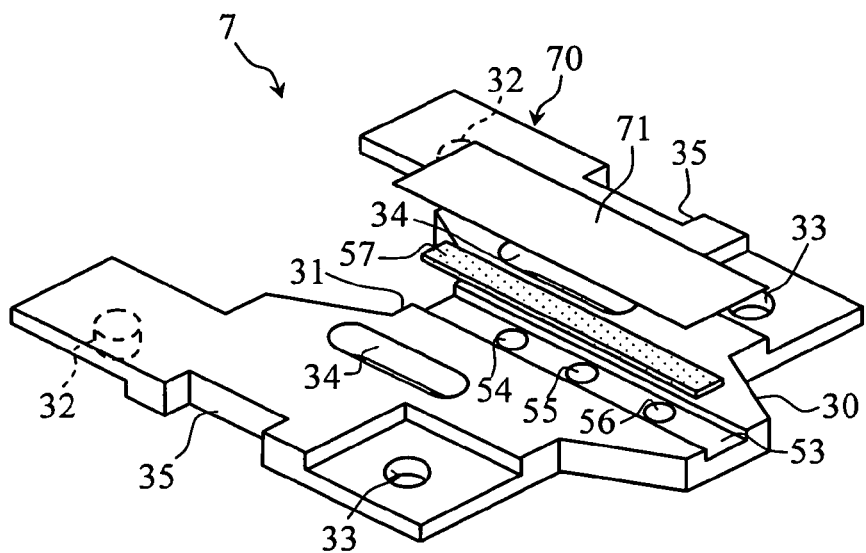
FIG. 22B is an exploded perspective view thereof.

A biosensor 7 shown in FIGS. 22A and 22B includes a base 70 and a cover sheet 71.

The base 70 has the projecting portion 30, the recessed portion 31, the pair of engagement projections 32, the pair of engagement holes 33, the pair of through-holes 34, the cutout 35, and the groove 53 integrally incorporated. The base 70 is further provided with the working electrode 54, the counter electrode 55, the detection electrode 56, and the reagent layer 57.

The cover sheet 71 is joined to cover the groove 53. Thus, the cover sheet 71 and the groove 53 define the capillary 36. The cover sheet 71 is made of transparent resin film and the like, so that the movement state of the sample such as blood in the capillary 36 can be checked.

In such a biosensor 7, the projecting portion 30, the recessed portion 31, the pair of engagement projections 32, the pair of engagement holes 33, the pair of through-holes 34, and the groove 53 can be incorporated by resin molding, and the working electrode 54, the counter electrode 55, and the detection electrode 56 can be formed by insert molding. Thereafter, the reagent layer 57 is formed in the groove 53, and the groove 53 is covered by the cover sheet 71 to thereby obtain the biosensor 7. The biosensor 7 thus can be very easily manufactured.

The present invention is not limited to the above embodiments, and various modifications may be made. For instance, the present invention is not limited to a biosensor configured as an electrode type, and is applicable even to a cartridge accommodating a plurality of biosensors configured as a colorimetric type. The present invention is also not limited to the biosensor and is also applicable to other analyzing tools.

Furthermore, the means for coupling the plurality of biosensors in the cartridge is not limited to the combination of a through-hole and a projection, and may be other engagement methods.

In the present invention, the movable body for taking out the biosensor from the cartridge does not necessarily need to be integrated with the projection for pressing the biosensor. The biosensor also does not necessarily need to be pressed by the projection movable in the up and down direction.

The invention claimed is:

1. A cartridge comprising a plurality of analyzing tools including at least a first analyzing tool and a second analyzing tool arranged lined in a plane direction, and a case for accommodating the plurality of analyzing tools, the cartridge being configured to have each of the plurality of analyzing tools taken out one at a time from the case; wherein
the first analyzing tool includes a projecting portion projecting out in a thickness direction of the plurality of analyzing tools,
the second analyzing tool includes a recessed portion with which the projecting portion of the first analyzing tools engages, and
the second analyzing tool is arranged adjacent to the first analyzing tool in the plane direction.

2. The cartridge according to claim 1, further comprising holding means for putting one of the analyzing tools to be taken out in standby at a target position.

3. The cartridge according to claim 2, wherein the holding means includes a cutout portion arranged in the one of the analyzing tools to be taken out, and a hook arranged in the case.

4. The cartridge according to claim 1, wherein each of the plurality of analyzing tools includes an engagement portion having a surface opposite to a load in a direction in which each of the plurality of analyzing tools is configured to be taken out from the cartridge.

5. The cartridge according to claim 4, wherein the engagement portion is a through-hole.

6. The cartridge according to claim 4, wherein the case includes a slit through which an acting body is inserted, the acting body engaging with the engagement portion and putting the load in the direction in which each of the plurality of analyzing tools is configured to be taken out from the cartridge.

7. The cartridge according to claim 1, wherein the case further includes a recessed portion for allowing displacement of a position in the thickness direction of the analyzing tool when the analyzing tool is relatively moved in a take-out direction with respect to the case.

8. An analyzing system comprising:
a cartridge having a plurality of analyzing tools arranged lined in a plane direction accommodated in a case; and
an analyzer, to which the cartridge is attached, for analyzing a sample using the analyzing tool taken out from the cartridge; wherein
the plurality of analyzing tools include at least a first analyzing tool and a second analyzing tool, the first analyzing tool including a projecting portion projecting out in a thickness direction of the plurality of analyzing tools and the second analyzing tool including a recessed portion with which the projecting portion of the first analyzing tools engages, the second analyzing tool being arranged adjacent to the first analyzing tool in the plane direction,
each of the plurality of analyzing tools includes an engagement portion having a surface opposite to a load in a direction in which each of the plurality of analyzing tools is configured to be taken out from the cartridge; and
the analyzer includes an acting body engaging with the engagement portion and putting the load on the engagement portion in a direction in which the analyzing tool is taken out from the cartridge.

9. The analyzing system according to claim 8, wherein the acting body reciprocates in the thickness direction of the analyzing tool, and is configured to select a state the load can be acted on the engagement portion and a state the load cannot be acted.

10. The analyzing system according to claim 9, wherein the engagement portion is a engagement recessed portion, and the acting body is an engagement projecting portion.

11. The analyzing system according to claim 10, wherein the engagement recessed portion is a through-hole, and the engagement projecting portion is a pin.

12. The analyzing system according to claim 8, wherein the case further includes a recessed portion allowing displacement of a position in the thickness direction of the analyzing tool when the analyzing tool is relatively moved in a take-out direction with respect to the case; and the analyzer further includes a pressing body for pressing the analyzing tool in the thickness direction and holding the analyzing tool.

13. The analyzing system according to claim 12, wherein the pressing body is movable in the thickness direction with the acting body.

* * * * *